(12) United States Patent
Marriott et al.

(10) Patent No.: US 10,259,837 B2
(45) Date of Patent: Apr. 16, 2019

(54) METHOD OF SEPARATING RHAMNOLIPIDS FROM A FERMENTATION BROTH

(71) Applicant: Conopco, Inc., Englewood Cliffs, NJ (US)

(72) Inventors: Raymond John Marriott, Kettering (GB); Paul Simon Stevenson, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/552,661

(22) PCT Filed: Feb. 25, 2016

(86) PCT No.: PCT/EP2016/053982
§ 371 (c)(1),
(2) Date: Aug. 22, 2017

(87) PCT Pub. No.: WO2016/139127
PCT Pub. Date: Sep. 9, 2016

(65) Prior Publication Data
US 2018/0044364 A1    Feb. 15, 2018

(30) Foreign Application Priority Data
Mar. 2, 2015 (EP) .................................. 15157241

(51) Int. Cl.
| | | |
|---|---|---|
| *C07H 1/08* | (2006.01) |
| *B01D 11/04* | (2006.01) |
| *B01D 15/00* | (2006.01) |
| *B01J 20/14* | (2006.01) |
| *C07H 15/04* | (2006.01) |
| *C07H 15/06* | (2006.01) |

(52) U.S. Cl.
CPC ............ *C07H 1/08* (2013.01); *B01D 11/0403* (2013.01); *B01D 15/00* (2013.01); *B01J 20/14* (2013.01); *C07H 15/04* (2013.01); *C07H 15/06* (2013.01)

(58) Field of Classification Search
None
See application file for complete search history.

(56) References Cited

U.S. PATENT DOCUMENTS

| | | | |
|---|---|---|---|
| 2,182,306 | A | 12/1939 | Ulrich |
| 2,208,095 | A | 7/1940 | Easelmann et al. |
| 2,553,696 | A | 5/1951 | Wilson |
| 2,806,839 | A | 9/1957 | Crowther et al. |
| 3,033,746 | A | 5/1962 | Moyle et al. |
| 5,578,563 | A | 11/1996 | Trinh et al. |
| 5,656,747 | A | 8/1997 | Mixich et al. |
| 2012/0322751 | A1 | 12/2012 | Piljac |
| 2014/0086864 | A1 | 3/2014 | Ishimori et al. |

FOREIGN PATENT DOCUMENTS

| | | |
|---|---|---|
| CN | 101407831 | 4/2008 |
| DE | 4237334 | 5/1994 |
| DE | 19648439 | 5/1998 |
| DE | 102009046169 | 5/2011 |
| EP | 0317036 | 5/1989 |
| EP | 0975718 | 2/2000 |
| EP | 1411111 | 4/2004 |
| EP | 1445302 | 8/2004 |
| EP | 2410039 | 1/2012 |
| WO | WO9838270 | 9/1998 |
| WO | WO2006086492 | 8/2006 |
| WO | WO2011117427 | 9/2011 |
| WO | WO2011120776 | 10/2011 |
| WO | WO2012010406 | 1/2012 |
| WO | WO2012156250 | 11/2012 |
| WO | WO2013043857 | 3/2013 |
| WO | WO2014095367 | 6/2014 |
| WO | WO2014118095 | 8/2014 |
| WO | WO2014173659 | 10/2014 |

OTHER PUBLICATIONS

Supercritical CO2: A green Solvent, Chemical Engineering, Feb. 1, 2010, http://www.chemengonline.corn/supercritical-co2-a-green-solvent.*
Novik, Journal of Biotechnology 121 (2006) 555-562.*
Elhenshir, Energy Procedia 37 (2013) 6964-6978.*
Montanari, Journal of Supercritical Fluids 14 (1999) 87-93.*
Tena, Fresnius J Anal Chem (1998) 361:143-148.*
Heyd et al., Development and trends of biosurfactant analysis and purificaiton using rhamnolipids as an example, Analytical and Bioanalytical Chemistry, Mar. 6, 2008, pp. 1579-1590, 391-5 (NPL 1, pp. 1-12).
IPRP in PCTEP2016053982, dated Feb. 3, 2017 (NPL 1, pp. 13-26).
IPRP2 in PCTEP2016052680, dated May 19, 2017 (NPL 1, pp. 27-45).
Reiling et al., Pilot plant production of rhamnolipid biosurfactant by Pseudomonas aeruginosa, Applied and Environmental Microbiology, May 1986, pp. 985-989; XP055036395retrieved from internet: http://aem.asm.org/content/51/5/985.full.pdf, 51-5 (NPL 1, pp. 46-51).
Search Report & Written Opinion in PCTEP2016054025, dated Jun. 1, 2016 (NPL 1, pp. 52-62).
Search Report and Written Opinion in PCTEP2016052680, dated Apr. 18, 2016 (NPL 1, pp. 63-76).
Search Report and Written Opinion in PCTEP2016053982, dated May 17, 2016, WO (NPL 1, pp. 77-90).
Search Report and Written Opinion in EP15157240, dated Aug. 18, 2015 (NPL 2, pp. 1-5).
Search Report and Written Opinion in EP15157241, dated Jul. 24, 2015, EP (NPL 2, pp. 6-14).

(Continued)

*Primary Examiner* — Layla D Berry
(74) *Attorney, Agent, or Firm* — Greenberg Traurig, LLP (57) ABSTRACT

A method of extracting at least one rhamnolipid compound from a rhamnolipid fermentation mixture, the method comprising the steps of: (a) admixing an inert adsorbing support with a rhamnolipid fermentation mixture; (b) dissolving the mixture in an organic solvent at a temperature higher than 31° C. and at a pressure higher than 73 bars; (c) separating at least one fatty compound; (d) adding a co-solvent to said organic solvent; (e) modifying temperature and/or pressure; (f) separating a first rhamnolipid compound; and (g) separating a second rhamnolipid compound.

5 Claims, 7 Drawing Sheets

(56) References Cited

OTHER PUBLICATIONS

Search Report and Written Opinion in EP15157244, dated Aug. 26, 2015 (NPL 2, pp. 15-22).
Written Opinion 2 in PCTEP2016052680, dated Feb. 23, 2017 (NPL 2, pp. 23-29).
Co-pending Application Petkov et al, filed Aug. 22, 2017.
Co-pending Application Jones et al, filed Aug. 22, 2017.

* cited by examiner

METHOD OF SEPARATING RHAMNOLIPIDS FROM A FERMENTATION BROTH

This invention relates to the separation of rhamnolipid compounds from a rhamnolipid fermentation medium.

Biosurfactants such as rhamnolipids may be produced by means of fermentation using renewable biomass and various bacteria such as *Pseudomonas aeruginosa* or other suitable microbial organism, together with a feedstock which may be plant or animal oil or sugars.

However, the resultant fermentation mixture or 'broth' must be further processed to remove/purify rhamnolipid. Other broth constituents include incompletely reacted feed substrates such as tri-, di- and mono glycerides and also fatty acids as well as cell constituents and sugars etc. High recovery and purification costs are a major hurdle to overcome for the commercialisation of rhamnolipids on a large scale.

Heyd et al. (Anal. Bioanal. Chem. (2008) 391, 1579) provide a summary of biosurfactant analysis and purification. Railing et al. (Appl. Environ. Microbiol. (1986), 51(5), 985) disclose a pilot plant scale method of producing rhamnolipid biosurfactant using *Pseudomonas aeruginosa*. EP 0317036 discloses a method of preparing L-rhamnose, the method involving heating in an aqueous solution of organic carboxylic acid at low pH.

It is an object of the invention to provide an improved method of extracting rhamnolipid compounds from a fermentation mixture.

A detailed drescription of the invention is hereafter described with specific reference being made of the drawings in which.

Accordingly the invention provides a method of extracting at least one rhamnolipid compound from a rhamnolipid mixture, the method comprising the steps of:
(a) admixing an inert adsorbing support with a rhamnolipid mixture;
(b) dissolving the mixture in an organic solvent at a temperature higher than 31° C. and at a pressure higher than 73 bars;
(c) separating at least one fat compound;
(d) adding a co-solvent to said organic solvent;
(e) modifying temperature and/or pressure;
(f) separating a first rhamnolipid compound; and
(g) separating a second rhamnolipid compound.

With the invention, the process for harvesting rhamnolipid compounds is greatly improved in terms of efficacy, accuracy and environmental impact.

Preferably the rhamnolipid extraction of steps (f) and (g) follows addition of a co-solvent (d) and increase in temperature and/or pressure in step (e).

Preferably step (c) precedes steps (d) to (f). Preferably water is also removed in step (c).

Preferably the step (c) takes place with multiple extraction/separation vessels in parallel whereby water is separated in one vessel and fat compounds are separated in a separate vessel.

Preferably the defatting step (c) is prolonged until virtually no oil or water is extracted.

Preferably the steps are alphabetically sequential.

Preferably the pressure is decreased in step (e). Preferably this is sufficient to provide a phase change in the organic solvent. In the case of $CO_2$, this pressure decrease should be sufficient to convert super critical $CO_2$ to liquid $CO_2$.

Preferably multiple extraction/separator vessels are used for steps (f) and (g).

In general, admixing and dissolving steps (a) and (b) precede steps (c) to (g). Steps (c) to (g) may be performed in any appropriate order. For example, the step (d) of adding cosolvent preferably precedes modifying the temperature and/or pressure in step (e). In some examples, separating a fat compound step (c) may follow steps (d) and (e).

In step (e), the temperature may be increased or decreased, and the pressure maintained. Alternatively, the temperature may be maintained and the pressure increased or decreased. Alternatively, the temperature and pressure may be increased, or the temperature and pressure may be decreased. Alternatively, one of the temperature and pressure may be increased, and the other of the temperature and pressure may be decreased.

Preferably, the temperature and pressure are increased in step (e). Alternatively, preferably the temperature is maintained and the pressure is reduced in step (e).

Preferably the first rhamnolipid compound comprises a mono-rhamnolipid (commonly referred to as "R1").

Preferably the second rhamnolipid compound comprises a di-rhamnolipid (commonly referred to as "R2").

As used herein the term "rhamnolipid mixture" means the post microbial fermentation mixture of rhamnolipids, fatty acids and glycerides including monoglycerides, triglycerides, diglycerides and sugars, protein, residual cells/cell material. This may comprise the rhamnolipid fermentation broth or crude product or rhamnolipid-rich phase of a rhamnolipid fermentation broth following other processing.

As used herein the term "inert adsorbing support" may comprise a single structure or an array of structures. The term "inert adsorbent" may alternatively be used interchangeably with the term "inert adsorbing support" as used herein.

Preferably the inert adsorbing support comprises a large surface area and is has a porous structure (high porosity). Said porosity may be provided inherently by the support structure (such as one or more bodies comprising multiple pores) and/or by the configuration of an array of structures (such as an array of beads or balls or particles in a free flowing powder form wherein said particles themselves may also comprise pores).

Preferably the inert adsorbing support comprises diatomaceous earth.

Preferably the inert adsorbing support comprises Celite. Preferably, the Celite may comprise Celite S®, Celite 110®, Celite 209®, Celite 281®, Celite 503®, Celite 512M®, Celite 545®, Celite 545AW®, Celite 560®, Celite 577F®, Celite 535® all produced by Celite Corp.

Preferably the inert adsorbing support material has pores having a diameter ranging from 7.5 to 30 nm. Preferably the porosity ranges from 1 to 4 $cm^3/g$. Preferably the specific surface area ranges between 5 to 250 $m^2/g$. Preferably in the case of a particulate inert adsorbing support material, the average particle diameter is in the range 1 μm to 1.5 mm.

In the case of a free flowing particulate inert adsorbing the amount of loading of the mixture onto the support is preferably between 5 wt % and 60 wt % based on the weight of the loaded powder. Preferably it ranges between 20 wt % and 55 wt % and more preferably between 30 wt % and 50 wt %.

The rhamnolipid mixture is preferably adsorbed onto the inert adsorbing support in aqueous form.

Preferably the organic solvent is carbon dioxide ($CO_2$). The carbon dioxide, by means of steps (b) and (e) is in the supercritical state. Preferably it is in a supercritical state for both (b) and (e).

For separation using carbon dioxide in the supercritical state, the separation reaction is carried out at a temperature higher than 31° C. and at a pressure higher than 73 bars. Preferably the temperature ranges between 31° C. and 200° C., more preferably between 31° C. and 80° C. Preferably the pressure ranges between 73 bars and 1100 bars, more preferably between 200 bars and 700 bars. Solvents other than carbon dioxide are contemplated. In some cases, step (b) may occur at other temperatures and pressures. In that case, step (b) may comprise dissolving the mixture in an organic solvent.

Most preferably steps (a) to (d) are performed at a pressure of 450 bar and temperature 40° C. and step (e) the pressure is modified by reducing to 300 bar (with temperature maintained at 40° C.) so that steps (f) and (g) are carried out at a reduced pressure versus steps (a) to (d).

The co-solvent preferably comprises an alcohol. The co-solvent preferably comprises ethanol or methanol. The co-solvent most preferably comprises ethanol (e.g. IMS: industrial methylated spirit).

Preferably the amount of co-solvent used is increased to remove different rhamnolipid compounds. The amount of co-solvent is preferably increased from 2.5 to 10 weight % (of total solvent weight) to remove mono-rhamnolipid and di-rhamnolipid gradually.

Preferably the amount of co-solvent used is 2.5 wt. % for mono-rhamnolipid removal. Preferably the amount of co-solvent used is 10 wt. % for di-rhamnolipid removal. Preferably the amount of co-solvent used is 5 wt. % for removal of a mixture of mono-rhamnolipid and di-rhamnolipid.

EXAMPLES

Figure 1:
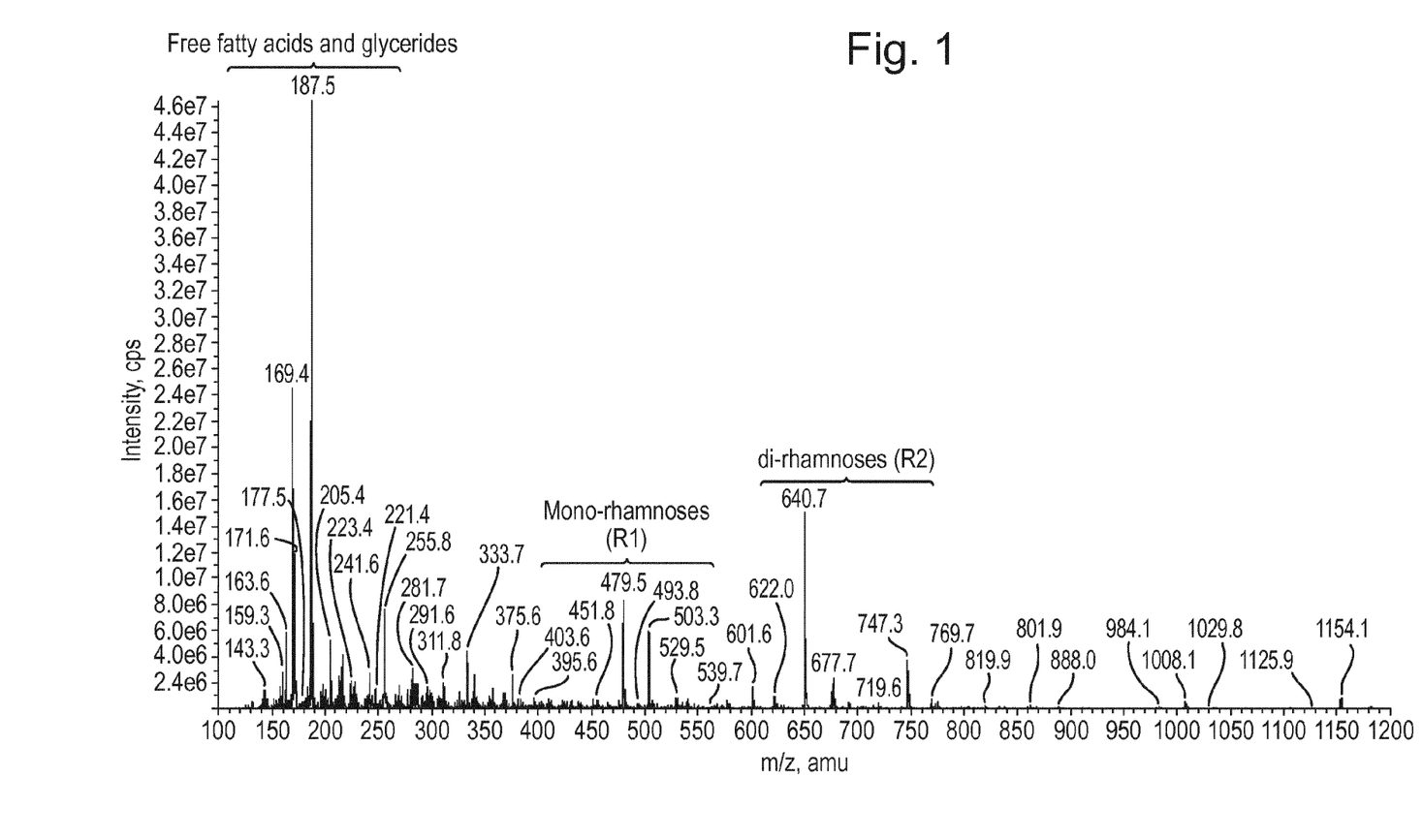
FIG. 1 shows extraction trials using crude rhamnolipid biomass of composition identified by mass spectrometry.

Extraction trials using crude rhamnolipid biomass of composition identified by mass spectrometry shown in FIG. 1. Mass spectrometry analysis was carried out after preparing solutions at 30 mg/L in methanol. Analysis was carried out with an Electrospray Ionisation (ESI) in negative ionization mode, scanning in the range of 100-1200 amu, with a flow rate of 20 μL/min. In FIG. 1 we can see the different compounds: fatty acids and glycerides, monorhamnoses (R1) and dirhamnoses (R2)

A commercial sample of rhamnolipid JBR 425 ex Jeneil previously stored at 4° C. was mixed with inert adsorbing support: diatomaceous earth as Celite 545 (ex Celite Corp in a ratio 3.7 parts support to 1 part rhamnolipid mixture.

Extraction was via supercritical fluid chromatography using a Thar SFC-1000 fitted with 1 L extractors and also on a Separex pilot plant separex 2×16 L using the full volume (16 L) of both extractors in parallel.

The extractor was filled with the supported rhamnolipid mixture. The extraction consisted in two steps: a dewatering/defatting step using supercritical $CO_2$ without cosolvent and a fractionation step to remove mono- and di-rhamnolipid compounds with supercritical $CO_2$ and increasing proportions of cosolvent.

The defatting step was prolonged until virtually no oil or water was extracted. In the first step (supercritical without cosolvent), the first separator contained mainly the free fatty acids and the second separator contained the water. In the supercritical plus cosolvent step, the existence of two separators also enhanced the fractionation.

Results And Analysis

| Yields of Extraction | | | | |
|---|---|---|---|---|
| Fraction | Content | Yield (%) | Co-solvent | Kg $CO_2$/Kg Raw Mat |
| 0 (not sent) | water | 28 | 0 | — |
| 1 | fatty acids | 16 | 0 | 36 |
| 2 | R1 | 1.5 | 2.5 | 8 |
| 3 | R1 + R2 | 4 | 5 | 8 |
| 4 | R2 | 11 | 10 | 8 |

Figure 2:
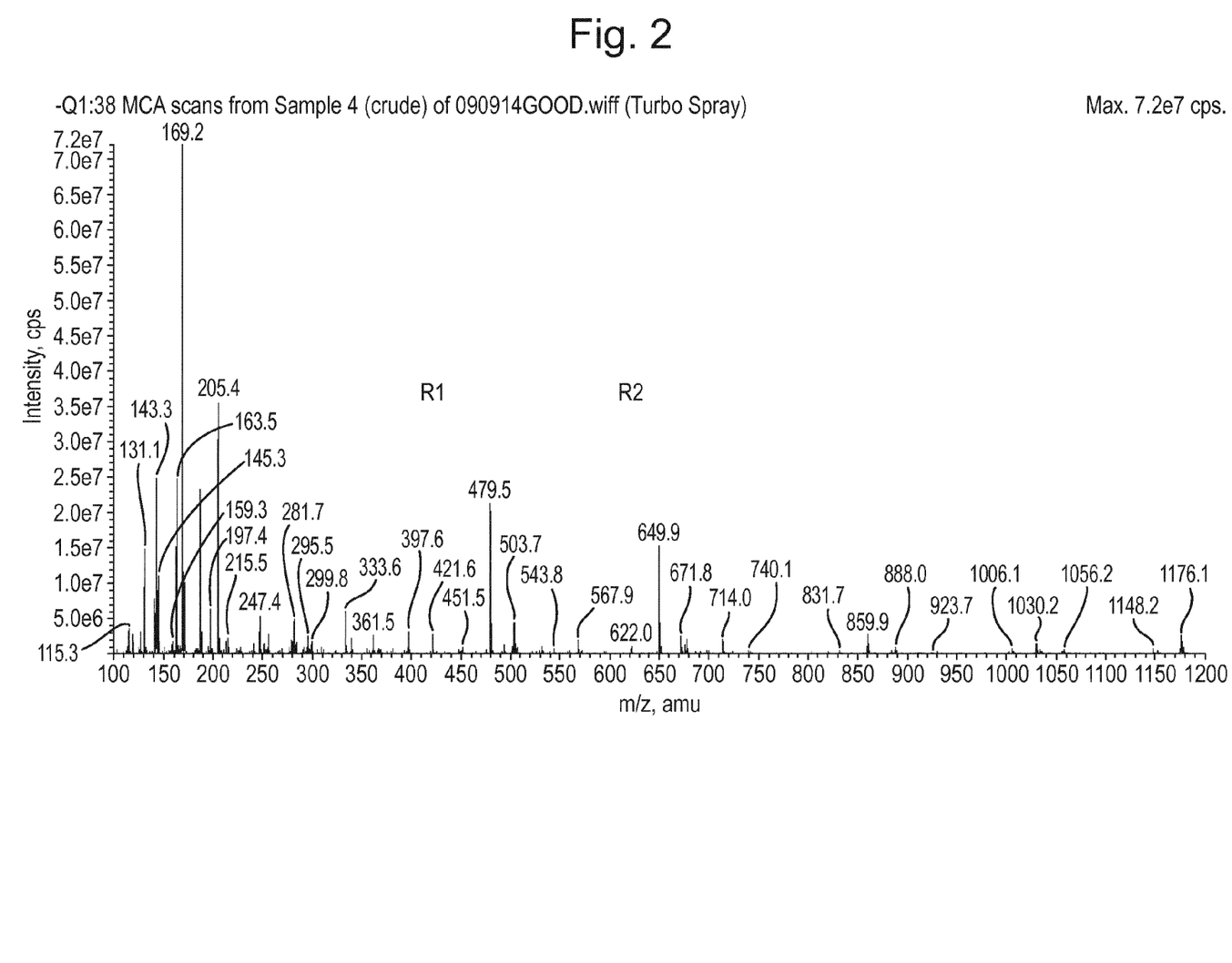
FIG. 2 shows results per fraction for Sample 4, Sample 7, and Sample 5 by mass spectrometry.
Figure 3:
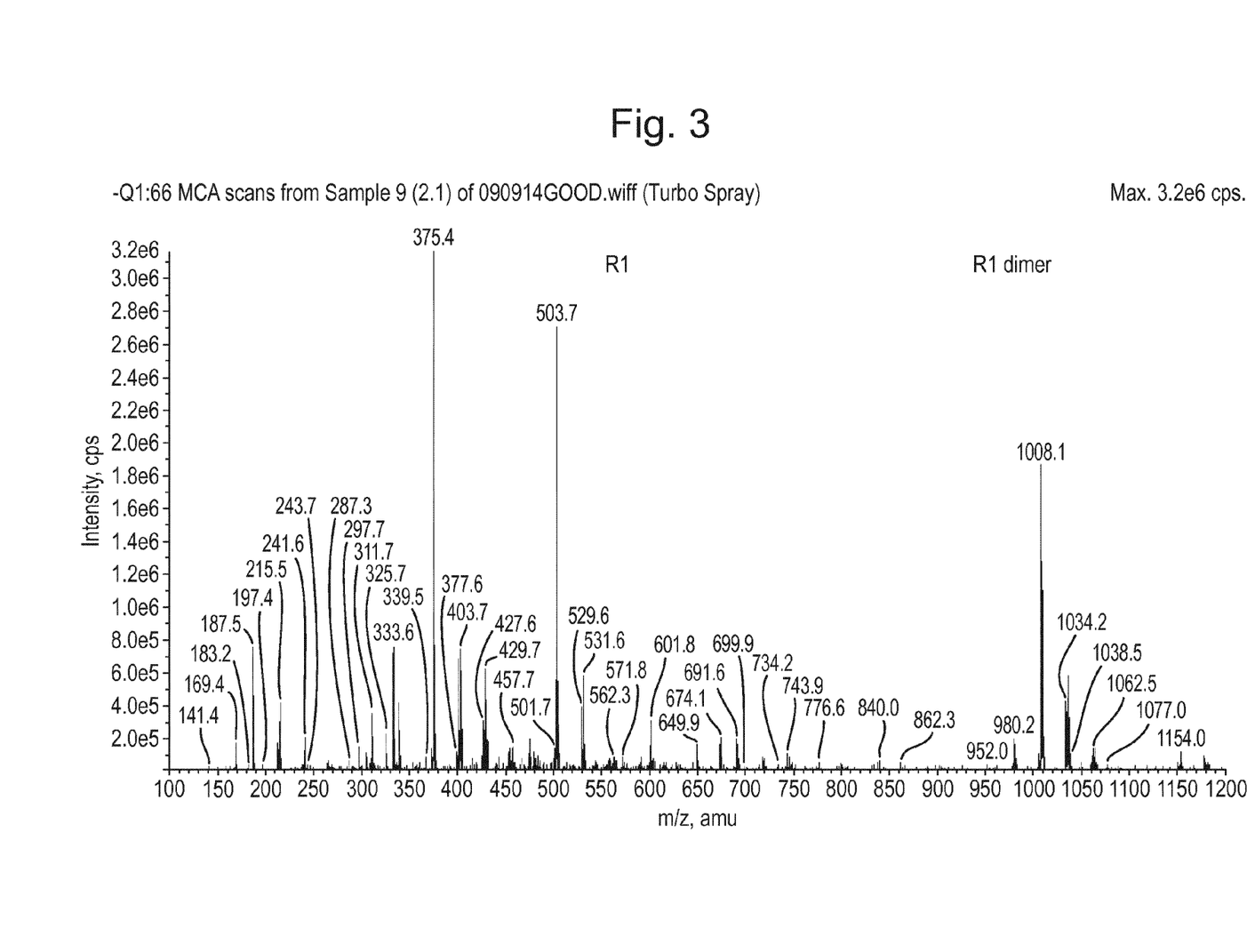
FIG. 3 shows results per fraction for Sample 9 and Sample 13 by mass spectrometry.

Mass spectrometry and ESI analysis was conducted on the fractions according to the method above described. FIGS. 2 and 3 show the results per fraction.

The invention claimed is:

1. A method of extracting at least one rhamnolipid compound from a rhamnolipid fermentation mixture, the method comprising the alphabetically sequential steps of:
   (a) admixing an inert adsorbing support with a rhamnolipid fermentation mixture;
   (b) dissolving the mixture in an organic solvent at a temperature higher than 31° C. and at a pressure higher than 73 bars;
   (c) separating at least one fatty compound;
   (d) adding a co-solvent to the organic solvent;
   (e) decreasing the pressure of the co-solvent and the organic solvent sufficiently so as to result in a phase change in the organic solvent;
   (f) separating a first rhamnolipid compound; and
   (g) separating a second rhamnolipid compound wherein in step (b), the organic solvent is in a supercritical state; and
   wherein the organic solvent is carbon dioxide.

2. A method according to claim 1 wherein the first rhamnolipid compound comprises a mono-rhamnolipid.

3. A method according to claim 1 wherein the second rhamnolipid compound comprises a di-rhamnolipid.

4. A method according to claim 1 wherein the inert adsorbing support comprises diatomaceous earth.

5. A method according to claim 1 wherein the co-solvent comprises an alcohol.

* * * * *